United States Patent
Werder et al.

(10) Patent No.: US 8,355,789 B2
(45) Date of Patent: Jan. 15, 2013

(54) METHOD AND APPARATUS PROVIDING ASYNCHRONOUS NEURAL STIMULATION

(75) Inventors: Jon Werder, Corcoran, MN (US); Jonathon E. Giftakis, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1246 days.

(21) Appl. No.: 11/414,141

(22) Filed: Apr. 28, 2006

(65) Prior Publication Data

US 2008/0046052 A1 Feb. 21, 2008

(51) Int. Cl.
*A61N 1/18* (2006.01)

(52) U.S. Cl. .............................. 607/45; 607/73

(58) Field of Classification Search ................ 607/46, 607/48, 62, 73, 2, 45
See application file for complete search history.

(56) References Cited

U.S. PATENT DOCUMENTS

| | | | |
|---|---|---|---|
| 2,350,797 A | 6/1944 | Morland et al. |
| 3,489,152 A | 1/1970 | Barbara |
| 3,650,277 A | 3/1972 | Sjostrand et al. |
| 3,954,111 A | 5/1976 | Sato |
| 3,983,881 A | 10/1976 | Wickham |
| 4,121,594 A | 10/1978 | Miller et al. |
| 4,153,059 A | 5/1979 | Fravel et al. |
| 4,210,151 A | 7/1980 | Keller, Jr. |
| 4,338,945 A | 7/1982 | Kosugi et al. |
| 4,390,023 A | 6/1983 | Rise |
| 4,431,000 A | 2/1984 | Butler et al. |
| 4,541,432 A | 9/1985 | Molina-Negro et al. |
| 4,556,064 A | 12/1985 | Pomeranz et al. |
| 4,686,991 A | 8/1987 | Dufresne et al. |
| 4,699,143 A | 10/1987 | Dufresne et al. |
| 4,706,674 A | 11/1987 | Dieken et al. |
| 4,887,603 A | 12/1989 | Morawetz et al. |
| 4,922,908 A | 5/1990 | Morawetz et al. |
| 5,069,211 A | 12/1991 | Bartelt et al. |
| 5,269,304 A | 12/1993 | Matthews |
| 5,683,422 A | 11/1997 | Rise |
| 5,755,749 A | 5/1998 | Sakano |
| 5,792,212 A | 8/1998 | Weijand |
| 6,188,929 B1 | 2/2001 | Giordano |
| 7,050,856 B2 * | 5/2006 | Stypulkowski ............ 607/45 |

(Continued)

FOREIGN PATENT DOCUMENTS

EP 0 099 662 A1 2/1984

(Continued)

OTHER PUBLICATIONS

Giftakis et al., PC operating system for measuring discrete biological responses during classical conditioning, Behavior Research Methods, Instruments, & Computers, 1997, 29 (4) 484-495.

(Continued)

*Primary Examiner* — Carl H Layno
*Assistant Examiner* — Pamela M Bays
(74) *Attorney, Agent, or Firm* — IPLM Group, P.A.

(57) ABSTRACT

Method and apparatus providing asynchronous neural stimulation pseudo-randomly varying at least one of a plurality of stimulation parameters. Neural stimulation may be monitored and compared with a target. Parameters may be varied to more closely match stimulation target. A range for at least one parameter may be established and the parameter varied within the range. A finite sequence of values within the range may be generated or selected. An average of the finite sequence of values may approximate the stimulation target.

13 Claims, 5 Drawing Sheets

U.S. PATENT DOCUMENTS

| | | |
|---|---|---|
| 2002/0055762 A1 | 5/2002 | Gliner |
| 2003/0093130 A1 | 5/2003 | Stypulkowski |
| 2003/0135248 A1 | 7/2003 | Stypulkowski |
| 2004/0034394 A1 * | 2/2004 | Woods et al. .................. 607/46 |
| 2005/0113882 A1 | 5/2005 | Cameron et al. |
| 2006/0069415 A1 | 3/2006 | Cameron et al. |

FOREIGN PATENT DOCUMENTS

| | | |
|---|---|---|
| EP | 0 033 643 B1 | 4/1984 |
| EP | 0 160 753 B1 | 11/1985 |
| EP | 0 171 881 A1 | 2/1986 |
| EP | 0 354 578 A2 | 2/1990 |
| EP | 0 911 061 A2 | 4/1999 |
| EP | 0 911 061 A3 | 11/1999 |
| EP | 1 145 736 A2 | 10/2001 |
| EP | 1 145 736 A3 | 4/2004 |
| GB | 2 163 355 A | 2/1986 |
| GB | 2 255 719 A | 11/1992 |
| WO | WO 02/30509 A2 | 4/2002 |
| WO | WO 02/30509 A3 | 4/2002 |
| WO | WO 03/059441 A1 | 7/2003 |

OTHER PUBLICATIONS

International Search Report for PCT/US2007/001773.

* cited by examiner

METHOD AND APPARATUS PROVIDING ASYNCHRONOUS NEURAL STIMULATION

FIELD OF THE INVENTION

The present invention generally relates to devices and methods for electrically stimulating biological tissue and, more particularly, to such devices and methods whose electrical stimulation is varied over time.

BACKGROUND

Nervous system disorders affect millions of people, sometimes causing death or degradation of life. Central and peripheral nervous system disorders include epilepsy, Parkinson's disease, essential tremor, dystonia, and multiple sclerosis (MS). Other nervous system disorders include mental health and psychiatric disorders, which also affect millions of individuals and include anxiety (such as general anxiety disorder, panic disorder, phobias, post traumatic stress disorder (PTSD), and obsessive compulsive disorder (OCD)), mood disorders (such as major depression, bipolar depression, and dysthymic disorder), sleep disorders (narcolepsy), obesity and anorexia.

Epilepsy is the most prevalent serious neurological disease across all ages. Epilepsy is a group of neurological conditions in which a person has or is predisposed to recurrent seizures. A seizure is a clinical manifestation of neurological activity indicative of a nervous system disorder, and results from excessive, hypersynchronous, abnormal electrical or neuronal activity in the brain. This electrical excitability of the brain may be likened to an intermittent electrical overload that manifests with sudden, recurrent and transient changes of mental function, sensations, perceptions and/or involuntary body movement. Because seizures are unpredictable, epilepsy affects a person's employability, psychosocial life and ability to perform otherwise standard tasks such as operating vehicles or heavy equipment.

Over time seizure repetition may result in neuronal cell loss at or near the seizure focus (such as with hippocampal sclerosis) and the neuronal network involved in seizure propagation. If the cell loss is significant, the firing patterns of the neural network may change, becoming less complex and/or chaotic. Such loss of irregularity in neuronal network firing patterns has been postulated to give rise to seizures.

Treatment therapies for epilepsy and other nervous system disorders can include any number of possible modalities alone or in combination including, for example, electrical stimulation, magnetic stimulation, drug infusion, and/or brain temperature control.

Devices and methods to therapeutically stimulate the body, e.g., the human body, are well known in the art. Some of these devices and methods vary, at least to some degree, the electrical stimulation provided.

Some devices and methods have multiple stimulation sites and modification which stimulation sites are activated at any given time. For example, U.S. Pat. No. 4,390,023, Rise, Patterned Electrical Tissue Stimulator, Medtronic, Inc., discloses a patterned electrical tissue stimulator includes a current source and analog multiplexers connected to an array of electrodes attached to the body. Microprocessor control of the multiplexer and the current source provides automatic selection of electrode stimulation pairs whereby spatial patterns of electrical stimulation are produced. Temporal summation and temporal patterns of electrical stimulus are provided through microprocessor control of the current source.

Also U.S. Pat. No. 4,556,064, Pomeranz et al, Electrotherapy Acupuncture Apparatus and Method, and European Publication No. EPO160753A1, European Application No. 84302741, Pomeranz et al, Electrotherapy Acupuncture Apparatus and Method, International Medical Machines, Inc., published Nov. 13, 1985, disclose a circuit for electrotherapy and electronic acupuncture, in which a pulse train is produced having negative pulses of a repetition rate of between 100 and 500 Hertz, arranged in groups having a repetition rate of between 1 and 50 Hertz. A positive bias is provided so that the integral of the pulse train signal is zero. The signal is randomly switched sequentially from one skin stimulus site to another with application times which can be adjusted between about 1 and 20 seconds (or more), to reduce or prevent brain habituation. Optionally there is a rest period between applications of the signal, in which no signal is applied to the skin sites.

Other devices and methods make at least one parameter of an electrical stimulation signal a function of another parameter. U.S. Pat. No. 4,887,603, Morawetz et al, Medical Stimulator With Stimulation Signal Characteristics Modulated as a Function of Stimulation Signal Frequency, Empi, Inc., and U.S. Pat. No. 4,922,908, Morawetz et al, Medical Stimulator With Stimulation Signal Characteristics Modulated as a Function of Stimulation Signal Frequency, Empi, Inc., disclose transcutaneous electrical nerve stimulation (TENS) apparatus which include first, second, and third oscillators. The first oscillator produces a first train of pulses at a main frequency. The second oscillator produces a second train of pulses at a modulation frequency. Output levels of the second train of pulses vary as a function of the modulation frequency. A frequency control simultaneously controls both the main and modulation frequencies. The third oscillator is responsive to the first and second oscillators and produces a third train of pulses at the main frequency. Intensity and frequency of the pulses of the third pulse train are modulated as a function of the output levels of the second train of pulses. An output driver responsive to the third oscillator converts the third train of pulses into a train of stimulation pulses having electrical characteristics adapted to be applied to a human body to suppress pain.

In another apparatus, electrical stimulation of the carotid sinus nerve is based upon a detected biological condition. U.S. Pat. No. 3,650,277, Sjostrand et al, Apparatus For Influencing the Systemic Blood Pressure in a Patient By Carotid Sinus Nerve Stimulation, LKB Medical AB, discloses a system for reducing and controlling the blood pressure of a hypertensive patient has electrical pulse stimulation of the carotid sinus nerves controlled by the arterial blood pressure of the patient in such a manner that the number of stimulation pulses within each heart cycle is determined by the arterial means blood pressure whereas the distribution of stimulation pulses over the heart cycle is a function of the arterial pulse wave shape with the pulse frequency being greater during the first portion of the heart cycle.

In still other devices and methods, electrical stimulation provided is varied according to predetermined criteria. U.S. Pat. No. 3,954,111, Sato, Electric Therapeutical Apparatus With Audio Frequency Band Alternating Current, discloses an electric therapeutic method and apparatus for medically treating diseases caused in the human body by utilizing natural phenomena that organisms including human being endowed with natural curative properties, that alternating current (generally referred to as biological electric current) is found in live cells and that the more active the vital action in cells, the more intensive biological current flows therein, through the introduction of alternating current into affected cells having abnormalities in their functions to activate the vital actions thereof, thereby enhancing the natural curative properties which such cells are originally endowed with. Also, U.S. Pat. No. 3,983,881, Wickham, Muscle Stimulator, Telectronics Pty., published Oct. 5, 1976, discloses an improved muscle stimulator, particularly suited to long term rhythmic stimulation for the selective development of musculature otherwise asymmetric or retarded in relative development. To minimize the subjects' awareness of stimulation, to permit nocturnal use, and to minimize battery consumption, the energy content of each pulse train is modulated by a progressive increase of pulse width up to a maximum, followed by a progressive decrease of pulse width, thus yielding a gradual contraction and relaxation of the muscle. U.S. Pat. No. 4,210,151, Keller, Jr., Electronic Pain Control With Scanned Output Parameters, Stimtech, Inc., discloses a device in which a first oscillator. dictates the pulse duration and frequency of stimulating signals; the oscillator output wave form is coupled to an output amplifier stage, and thence to the patient. A scanning oscillator provides a substantially linear ramp voltage, which in turn controls pulse duration, pulse frequency, and pulse intensity modulators. In turn, these modulators appropriately establish conditions within the first oscillator and the output stage whereby the output parameters are scanned through respective predetermined ranges, thereby periodically achieving optimum stimulating conditions.

Electrical stimulation may be determined by a predetermined formula. U.S. Pat. No. 5,755,749, Sakano, Change Control Method Using Three-Dimensional 1/F Fluctuation, Recording Medium Storing the Method, and Change Control Device Using Three-Dimensional 1/F Fluctuation, Toyo Sangyo Co., discloses a method for controlling changes in stimulation of every sort and kind including electrical stimulation, utilizes a three-dimensional 1/f fluctuation. The method is a change control method for controlling changes in stimulation to an object using a three-dimensional 1/f fluctuation and includes the steps of causing changes based upon 1/f fluctuation periods in the X-Z plane of a X-Y-Z space, causing changes based upon 1/f fluctuation periods in the X-Y plane of the space, superposing the caused changes of the previous steps, and applying the superposed caused changes to the object. This makes it possible to realize a low-frequency device free of problems attributable to the tolerance in neural response. A recording medium used to store the change control method, and a change control device using a three-dimensional 1/f fluctuation are also disclosed. Changes based on 1/f fluctuation periods in the X-Z plane and changes based on 1/f fluctuation periods in the X-Y plane are superposed on each other. In the case where stimulation is changed so as to avoid monotonous application of stimulation, for example, in a massaging device, it is possible to perform control for providing three-dimensional changes in the stimulation in which changes occur in both the vertical and horizontal directions, in addition to changes in the stimulation based on two-dimensional 1/f fluctuation periods at a single stimulation point. Thus, it becomes possible to effect control for stimulation changes which are natural and comfortable to an extent that they are closely correspond to the human physiology.

Still other devices and methods provide varied electrical stimulation in a variety of ways.

UK Published Patent Application No. 2 163 355A, Simonin, A Device For Aesthetic Skin Treatment, published Feb. 26, 1986, discloses a device for the aesthetic treatment of the skin and which essentially comprises a pulse generator, of which the positive and negative outputs are each connected to a plurality of fine solid skin penetrating needles which are fitted to the ends of respective flexible connecting wires. The device is applicable in particular to the treatment of the wrinkles of the skin of an individual. The needles are inserted into individual sockets inside insulating shrouds.

United States Published Patent Application No. 2002/0055762A1, Gliner, System and Method for Varying Characteristics of Electrical Therapy, U.S. Ser. No. 09/751,503, published May 9, 2002, discloses a system and method for providing percutaneous electrical nerve stimulation therapy to a patient. A method in accordance with one embodiment to the invention can include coupling an electrode to the recipient, applying electrical pulses to the probe, and varying a characteristic of the pulses applied to the recipient. For example, the pulses can be automatically varied from a value of no more than about 4 Hertz to a value of no less than about 10 Hertz and back over a period of greater than 6 seconds. The frequency variation can be repeated for a number of periods during the course of a session, or the frequency characteristics can change with subsequent periods. Characteristics of the electrical pulses can be changed depending on the duration of the session. The method for varying characteristics of the electrical pulses can be automatically implemented by a computer.

PCT Patent Application No. WO 02/30509A2, Gliner, System and Method For Varying Characteristics of Electrical Therapy, Vertis Neuroscience, discloses a system and method for providing electrical nerve stimulation therapy to a recipient. A system in accordance with one embodiment to the invention can include electrode means (such as a percutaneous electrode) coupleable to a recipient. The system can further included signal generating means for applying an electrical signal to the electrode means. The signal generating means can include frequency varying means for applying the electrical signal to the electrode means at a plurality of frequencies.

U.S. Pat. No. 2,350,797, Morland et al, Means For Producing Electric Impulses, discloses an apparatus for treatment of nerves and muscles by means of electric impulses, especially for artificial innervation of muscles, for instance for therapeutic purposes. The apparatus according to the invention is especially adapted for use in the training of muscles.

U.S. Pat. No. 4,121,594, Miller et al, Transcutaneous Electrical Nerve Stimulator, Med General, Inc., discloses a transcutaneous electrical nerve stimulator in which a unijunction transistor relaxation oscillator is used to produce variable frequency, variable width pulses. The relaxation oscillator drives a two stage transistor amplifier and the output therefrom is transformer coupled to a set of output electrodes which are adapted to be placed on the area of a patient to be treated. The amplitude of the signals applied to the patient as well as the rate and duration thereof are controllable so that the patient may adjust the nerve stimulation to suit his particular needs.

U.S. Pat. No. 4,153,059, Fravel et al, Urinary Incontinence Stimulator System, Minnesota Mining and Manufacturing Company, discloses a urinary incontinence stimulator system using an intra-anal electrode which provides a recurring series of pulses of varying duration and frequency to the electrode with each of such series of pulses spaced from the succeeding series by a rest period when no pulses are provided to the electrode.

U.S. Pat. No. 5,069,211, Bartelt et al, Microprocessor Controlled Electronic Stimulating Device Having Biphasic Pulse Output, Staodyn, Inc., discloses an electronic stimulating device is disclosed, with the stimulating device particularly illustrated being a transcutaneous nerve stimulating (TENS)

device for effecting suppression of pain by nerve fiber stimulation. Biphasic constant current output pulses are applied to a user through electrode pairs non-invasively positioned at the skin of the user. Microprocessor generated control pulses control generation of the biphasic output pulses at a biphasic output stage associated with each electrode pair, and the generated biphasic output pulses are capacitively coupled from each output stage which also includes a bleeder network for effecting capacitor discharge. Stimulation may be continuously applied at a level selected by the user or may be applied in timed varying intensities the maximum level of which is selectable, and displays of intensity and sensed faults, including low battery voltage, are also provided.

U.S. Pat. No. 5,269,304, Matthews, Electro-Therapy Apparatus, and British Patent No. 2255719A, Matthews, Electro-Therapy Apparatus, published Nov. 11, 1992, disclose an electro-therapy apparatus includes at least two electrodes adapted to feed oscillating current to selected sites on or beneath the epidermal or mucous surface remote from a treatment site. A common return electrode is provided at the treatment site which is subjected to the sum of the currents from the two feed electrodes. The feed electrodes may be contact feed electrodes or capacitative feed electrodes. The feed electrodes may operate at different frequencies so that the treatment site is stimulated by the beat frequency. This may be at or about 80 or 130 Hertz, if an anaesthetizing effect is required.

Still further, some devices and methods use a random or pseudo-random variation of electrical stimulation parameters.

U.S. Pat. No. 4,338,945, Kosugi et al, Method and Randomized Electrical Stimulation System For Pain Relief, Clinical Engineering Laboratory, discloses a system for generating electrical pulses for relieving the pain of the patient comprising a pulse generator and a controller for modulating the parameters of the output pulses of the pulse generator to fluctuate in accordance with the 1/f rule; i.e., the spectral density of the fluctuation varies inversely with the frequency.

U.S. Pat. No. 3,489,152, Barbara, Electrotherapeutic Apparatus With Body Impedance Sensitive Intensity Regulation, discloses an electrotherapeutic device embodying means for generating random, infrasonic and other varying signals, and applying the amplified signals to the human body for diagnostic and therapeutic purposes. The intensity of the applied signals is controlled by means responsive to changes in the impedance of the patient's body.

U.S. Pat. No. 4,431,000, Butler et al, Transcutaneous Nerve Stimulator With Pseudorandom Pulse Generator, Gatron Corporation, discloses an aphasias and other neurologically based speech and language impairments are treated by means of a transcutaneous electrical nerve stimulator. Preferably an irregular pulse train is applied by means of a pseudorandom pulse generator to the stimulator electrodes. The trapezoidal, monophasic pulses mimic typical physiological wave forms and the average pulse rate is in the order of the alpha rate. A series of pulses has a zero DC level which enables the nerves to repolarize, and a current source in the stimulator reduces the effects of such variables as skin resistance. The base pulse rate, pulse width and pulse amplitude can be adjusted to meet the particular needs of a patient.

U.S. Pat. No. 4,541,432, Moline-Negro et al, Electric Nerve Stimulator Device, Neurotronic Ltd., discloses an electric nerve stimulation device and apparatus for suppressing organic pain and other functional disorders of the nervous system without noxious sensation and substantially free from the adaptation phenomenon which usually results from subjecting receptors and nerve cells to uniform stimulating signals. The device includes a pulse generator to produce bipolar rectangular waveforms at preselected repetition rate and of a preselected width during a given first time period. Electronic circuits are connected to the post generator to deliver rectangular waveforms at a repetition rate which is chosen by a pseudo-random function for a second time period which is also chosen by a pseudo-random function. Further circuitry is provided to inhibit delivery of pulse waves for a third period of time. This third period of time is chosen by a pseudo-random function, thereby substantially eliminating noxious sensations and adaptation of nerve cells to stimulation during suppression of the organic pain. Electrodes are connected to the output of the device to apply the waveforms to nerve fibers to be stimulated thereby.

U.S. Pat. No. 5,683,422, Rise, Method and Apparatus For Treating Neurodegenerative Disorders By Electrical Brain Stimulation, Medtronic, Inc., discloses techniques for stimulating the brain to reduce the effects of neurodegenerative disorders by means of an implantable signal generator and electrode. A sensor is used to detect the symptoms resulting from the disorder. A microprocessor algorithm analyzes the output from the sensor in order to regulate the stimulation delivered to the brain.

U.S. Pat. No. 5,792,212, Weijand, Nerve Evoked Potential Measurement System Using Chaotic Sequences For Noise Rejection, Medtronic, Inc., discloses a measurement system for measuring signals evoked in response to stimulus pulses applied to a nerve, muscle or like physiological portion of a patient. The measurement system is characterized by delivering stimulus pulses at randomly generated intervals, and enabling the sense circuitry to track the timing of the stimulus pulse generation so as to aid in discriminating the evoked response pattern from surrounding noise. Specifically, after each stimulus pulse a delay is timed out for a time corresponding to the expected latency between the delivered pulse and the arrival of the evoked response at another location. The delay signal is then used to initiate time out of a window which controls operation of the sensing circuit for a window duration corresponding to when the evoked response pattern is appearing. Limiting the sensing operation to the window duration enables tracking of the response pattern, and minimizes power consumption. The sensed evoked response signals are further processed to provide control signals for adjustment of the delay and window, thereby optimizing the sensing operation. The measurement system is suitably part of a larger implantable stimulus system, which includes the ability to adjust pulse-to-pulse interval, or rate, and also pulse output level as a function of measured evoked response patterns. In a further embodiment, the stimulus system involves steering of stimulus pulses to selected nerve fibers or muscle tissue, and the measurement system provides feedback for adjusting the steering parameters.

U.S. Pat. No. 6,188,929, Giordano, Sequentially Generated Multi-Parameter Bioelectric Delivery System and Method, discloses a device and method for electro-stimulation. The user can select an overall treatment protocol of current frequencies and amplitudes to be applied for specified dwell periods defining a sweep cycle. The user can select for one or more periods in the cycle a frequency/amplitude to be applied to elicit a response such as a muscle contraction or the like. The device protocols may be selected to elicit responses while conserving power, to provide for heating without eliciting a response or to hop between frequency/amplitude combinations to produce the desired effect.

United States Published Patent Application No. 2003/0135248A1, Stypulkowski, Variation of Neural-Stimulation Parameters, U.S. Ser. No. 10/044,405, Medtronic, Inc., published Jul. 17, 2003, and PCT Published Patent Application WO 2003/059,441, Stypulkowski, Variation of Neural-Stimulation Parameters, Medtronic, Inc., disclose techniques for varying stimulus parameters used in neural stimulation to improve therapy efficacy, minimize energy consumption, minimize undesired side effects, and minimize loss of therapeutic effectiveness due to physiologic tolerance to stimulation. Neural stimulation is provided having a stimulation amplitude, a stimulation frequency, a stimulation pulse duration, an electrode-firing pattern, and a set of electrode-firing-polarity conditions. At least one of the stimulation parameters is pseudo-randomly varied. A second stimulation parameter is changed based upon having pseudo-randomly varied the first stimulation parameter and based upon a predetermined relationship specifying how changes in the first parameter affect desirable values for the second parameter.

Therapy directed to the network, which is capable of restoring complexity of network firing patterns, may be beneficial in preventing seizures. To achieve this, asynchronous electrical stimulation may be directed at the seizure focus site, or applied indirectly to nearby neurons connected via projection pathways (e.g. thalamus). The effect of asynchronous stimulation is twofold: to activate neurons that would otherwise remain silent; and, to increase the firing rate of existing neurons in the network.

BRIEF SUMMARY OF THE INVENTION

While the above-described devices and methods provide for a variance or variability in the electrical stimulation provided, it is difficult to determine the amount and/or type of stimulation actually provided to the patient due to the variations. As stimulation parameters are varied, particularly with random variations, the precise type, intensity, pulse width, etc., of stimulation that is being provided to the patient at any given point in time is difficult to determine and it is even more difficult to determine what stimulation has been provided to the patient over a period of time.

The randomness or the variability in stimulation parameters may enhance the therapeutic effect provided to the patient. However, such randomness or variability also inherently provides a disadvantage in specifying or determining the amount and/or type of stimulation provided to the patient.

The present invention provides devices and methods allowing for variations of electrical stimulation parameters, including random or pseudo-random variations, but still provides for the ability to provide a specific amount, value or type of stimulation provided to the patient over a period of time. The medical care provider can be confident that the patient will receive a known type or amount of electrical stimulation while still maintaining the advantageous results associated with variable stimulation, particularly random or pseudo-random variation of stimulation parameters.

In an embodiment, the present invention provides a method of providing neural stimulation having a target to a patient. Neural stimulation having a plurality of stimulation parameters is provided. At least one of the plurality of stimulation parameters is pseudo-randomly varied. Neural stimulation provided to the patient is monitored and compared with the target. An action is taken based thereon.

In an embodiment, at least one of the plurality of stimulation parameters is modified in order that the neural stimulation delivered to the patient more closely matches the target.

In an embodiment, a user is notified following monitoring.

In an embodiment, the present invention provides a method of providing neural stimulation having a target to a patient, the target determined, at least in part, by a plurality of stimulation parameters. Neural stimulation having a plurality of stimulation parameters is provided. At least one of the plurality of stimulation parameters is pseudo-randomly varied in a way to more closely match the target.

In an embodiment, an average of the finite sequence of values more closely matches the target than would occur randomly.

In an embodiment, an average of the finite sequence of values matches the target.

In an embodiment, the possible values for the values of the sequence of values are generated randomly and particular ones of the possible values are selected manually.

In an embodiment, the present invention provides a method of providing neural stimulation having a target to a patient, the target determined, at least in part, the a plurality of stimulation parameters. Neural stimulation specified by the plurality of stimulation parameters is provided to the patient. A range of at least one of the stimulation parameters over which at least one of the stimulation parameters may be varied with the target occurring within the range. Pseudo-randomly varying at least one of the plurality of stimulation parameters within the range in a way that more closely matches the target.

In an embodiment, at least one of the plurality of stimulation parameters is varied by generating a finite sequence of values of at least one of the plurality of stimulation parameters and selecting one of the finite sequence of values for the neural stimulation.

In an embodiment, an average of the finite sequence of possible values more closely matches the target than an average value taken between end points of the range.

In an embodiment, an average of the finite sequence of values approximates the target.

In an embodiment, one of the finite sequence of values is repeated selected during a stimulation treatment period.

In an embodiment, the selecting step is repeated during a stimulation treatment period.

In an embodiment, the generating step is performed randomly.

In an embodiment, the generating step is performed manually.

In an embodiment, the present invention provides an apparatus for providing neural stimulation having a target to a patient using a neural stimulator providing neural stimulation having a plurality of stimulation parameters. The neural stimulator pseudo-randomly varies at least one of the plurality of stimulation parameters. A monitor monitors the neural stimulation delivered to the patient. A comparator compares the neural stimulation delivered to the patient with the target. An action may be taken based upon a result from the comparator.

In an embodiment, at least one of the plurality of stimulation parameters is modified in order that the neural stimulation more closely matches the target.

In an embodiment, a communicator notifies a user of a result of the result from the comparator.

In an embodiment, the present invention provides an apparatus for providing neural stimulation having a target to a patient, the target determined, at least in part, by a plurality of stimulation parameters using a neural stimulator providing neural stimulation specified by the plurality of stimulation parameters. The neural stimulator pseudo-randomly varies at least one of the plurality of stimulation parameters to more closely match the target.

In an embodiment, the present invention provides an apparatus for providing neural stimulation having a target to a patient, the target determined, at least in part, by a plurality of stimulation parameters using a neural stimulator providing neural stimulation specified by the plurality of stimulation parameters. The neural stimulator pseudo-randomly varies at least one of the plurality of stimulation parameters in a way to more closely match the target. A range over which at least the one of the plurality of stimulation parameters may be varied is determined, the target occurring within the range. The neural stimulator pseudo-randomly varies at least one of the plurality of stimulation parameters in a way to more closely match the target.

In an embodiment, a finite sequence of values of at least one of the plurality of stimulation parameters is generated and one of the finite sequence of values is selected for the neural stimulation.

In an embodiment, an average of the finite sequence of values more closely matches the target than an average value taken between end points of the range.

In an embodiment, an average of the finite sequence of values approximates the target.

In an embodiment, an average of the finite sequence of values matches the target.

In an embodiment, one of the finite sequence of values is selected repeatedly during a stimulation period.

In an embodiment, the finite sequence of values is generated manually.

In an embodiment, possible values for the values of the sequence of values are generated randomly.

In an embodiment, at least one of the plurality of stimulation parameters is a parameter selected from the group consisting of an inter-stimulation interval, amplitude and pulse width.

DETAILED DESCRIPTION

Electrical neural stimulation uses electrical pulses, typically delivered using electrodes associated with the body of a person, to provide a particular function or result, typically treatment of a neural disorder such as epilepsy. Such neural stimulation sometimes involves stimulation using a pattern of electrical stimulation pulses. Electrical neural stimulation patterns can involve a number of stimulation parameters such as amplitude, either voltage or current or both, pulse width, number of pulses, stimulation duration and inter-stimulation interval. Such electrical neural stimulation is well known in the art, for example as discussed above in the Background section.

U.S. Patent Application Publication No. US2003/0135248, ("Stypulkowski '248"), Variation of Neural-Stimulation Parameters, assigned to Medtronic, Inc., discloses techniques for varying stimulus parameters used in neural stimulation to improve therapy efficacy, minimize energy consumption, minimize undesired side effects, and minimize loss of therapeutic effectiveness due to physiologic tolerance to stimulation, the content of which is hereby incorporated by reference in its entirety. Neural stimulation is provided having a stimulation amplitude, a stimulation frequency, a stimulation pulse direction, an electrode-firing pattern, and a set of electrode-firing-polarity conditions. At least one of the stimulation parameters is pseudo-randomly varied. A second stimulation parameter is changed based upon having pseudo-randomly varied the first stimulation parameter and based upon a predetermined relationship specifying how changes in the first parameter affect desirable values for the second parameter. The entire content of Stypulkowski is incorporated herein by reference.

Figure 1:
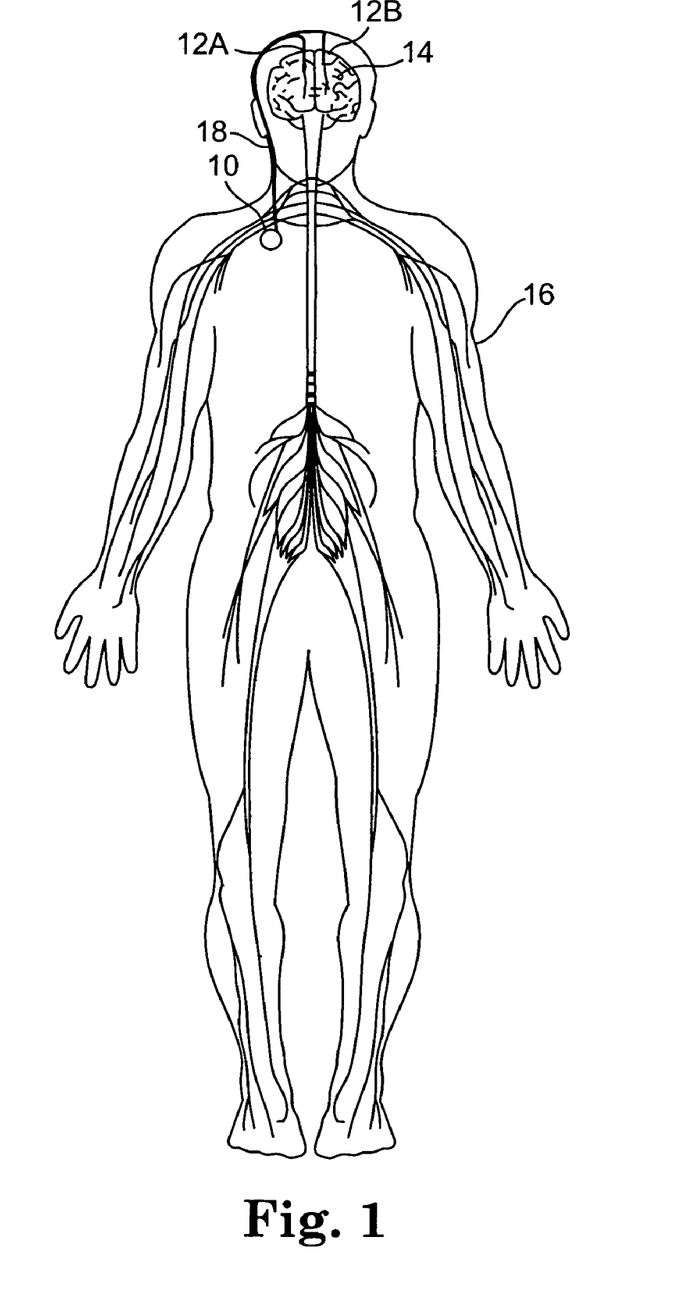
FIG. 1 illustrates an apparatus for providing neural stimulation implanted in the body of a patient with stimulation leads implanted in the brain of the patient.

Stypulkowski discloses both an apparatus and method for providing neural stimulation to improve therapy efficacy. FIG. 1 depicts a micro-processor controlled neural stimulation device 10. Device 10 is preferably implanted below the skin of a patient, or alternatively, may be an external device. Leads 12A and 12B are positioned to stimulate specific sites in the brain 14 of patient 16. Device 10 may take the form of a modified signal generator Model 7424 manufactured by Medtronic, Inc. under the trademark Itrel II. The distal end of leads 12A and 12B terminate in one or more stimulation electrodes generally implanted into a portion of the brain such as the thalamus, the internal capsule, the globus pallidus, the subthalmamic nucleus or other neural structure by conventional stereotactic surgical techniques. Any number of electrodes may be used for various applications. Each of the electrodes is individually connected to device 10 through leads 12A and 12B and conductor 18. Leads 12A and 12B are surgically implanted through a hole in the skull and conductor 18 is surgically implanted between the skull and the scalp.

As shown in FIG. 1, conductor 18 is divided into twin leads 12A and 12B that are implanted into brain 14 of patient 16 bilaterally. Alternatively, lead 12A and lead 12B may be supplied from a separate conductor and even from a separate signal generator. Further, dual leads 12A and 12B are shown for illustrative purposes only. Alternatively, device 10 may drive a single lead, such as lead 12A.

Figure 2:
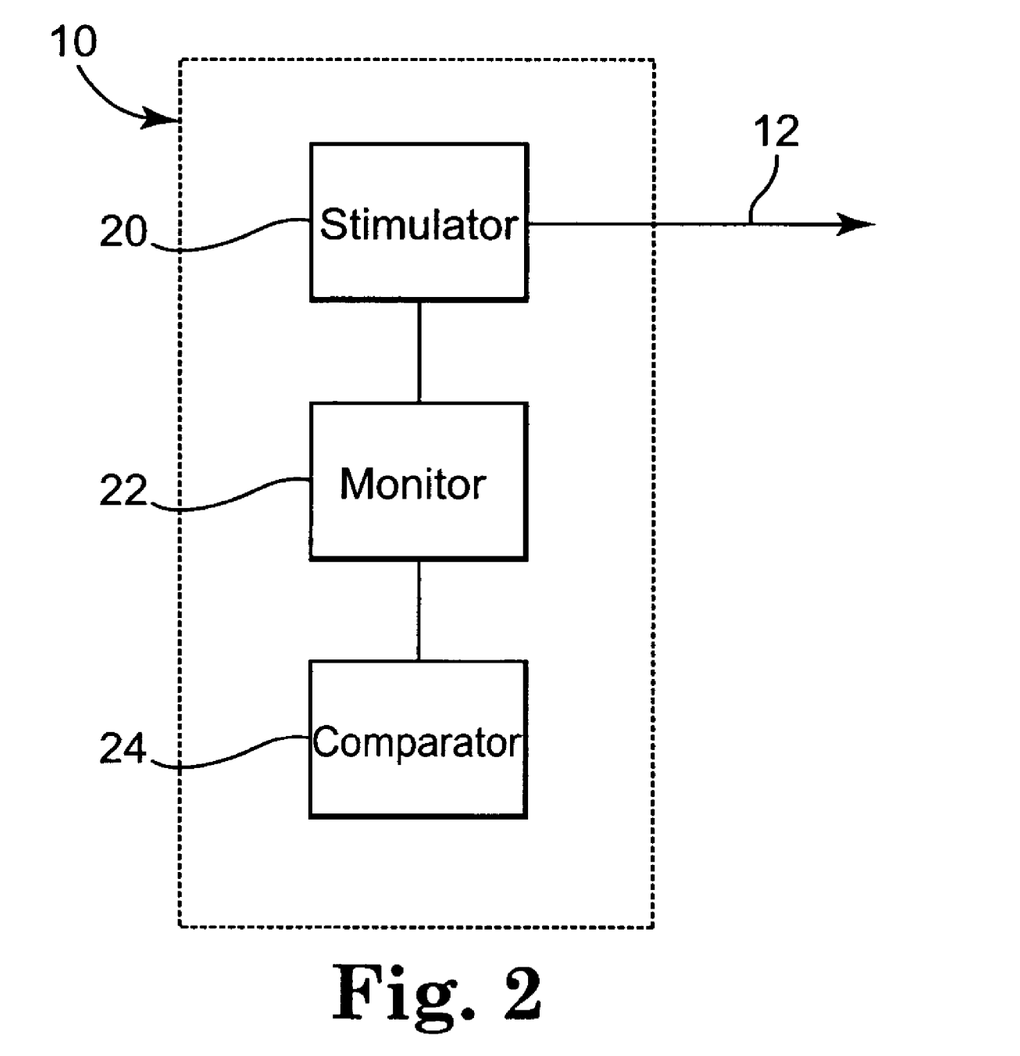
FIG. 2 is a general block diagram of an apparatus for providing neural stimulation.

FIG. 2 is a schematic block diagram of neural stimulation device 10, an apparatus for providing neural stimulation. Stimulator section 20 is conventional and provides electrical stimulation pulses through lead 12 to brain 14 of patient 16. Stimulator section 20 is well known in the art. An example of stimulator section 20 can be found in the description of Stypulkowski '248, previously incorporated by reference.

In general, stimulation section 20 generates a series of electrical stimulation pulses supplied through lead 12 to brain 14 of patient 16. Stimulator section 20 typically generates a series of electrical stimulation pulses, or pulse train. The electrical stimulation pulses can typically be varied by modifying or changing one or more stimulation parameters such as amplitude, either voltage amplitude or current amplitude, pulse width, the number of stimulation pulses in a series, the stimulation interval, such as the number of series of pulses provided or stimulation period, and inter-stimulation interval (ISI), the time between the end of one series of pulses, the commencement of a subsequent series of pulses, burst length, burst-to-burst interval, pulse start and pulse shape, as examples. Of course, many other characteristics of the electrical stimulation pulses can be specified and one or more of these other characteristics may also be specified as stimulation parameters.

Generally, a particular amount of electrical stimulation or a particular value of a stimulation parameter is desired to be prescribed for a particular patient 16. With such a prescription, stimulation section 20 may be set with one or parameters to provide electrical stimulation pulses with the prescribed value of such one or parameters. The value of such one or more parameters could be characterized as a target for the neural stimulation. It would be straight forward to achieve the target neural stimulation by simply setting the specified parameter to the prescribed value.

However, it has been suggested that varying one or more of the stimulation parameters of a series of electrical stimulation pulses can prove to be beneficial in some circumstances and may be more efficacious than simply repeating a non-varying series of stimulation pulses.

One technique for varying a stimulation parameter is to set a range, e.g., a minimum and a maximum, over which a particular stimulation parameter will be allowed to vary. A random or pseudo-random variation of that stimulation parameter would allow the prescribed electrical stimulation therapy to proceed with a variation in at least one stimulation parameter.

However, over a particular stimulation period, the randomness of such a random or pseudo-random variation in a stimulation parameter may lead to an inappropriate amount or value of electrical stimulation therapy actually provided to patient 16 over that particular stimulation period.

As an example, the target therapy may not be near the mean of the allowed range in variation of a stimulation parameter. For example, a stimulation parameter may be allowed to vary in a range of between a value of one and a value of ten. However, the target stimulation for such parameter may be seven. If this stimulation parameter is allowed to vary randomly between one and ten, a mean electrical stimulation with this parameter of seven generally will not be achieved. Further, even if the target stimulation provides for a value for this parameter that is at or near the mean of the value of the allowed range of such parameter, there is no guarantee that over any particular stimulation period, particularly a relatively short stimulation period, that the mean value of this parameter actually provided to patient 16 will equal or be near such mean. The randomness of the variation could lead to a different result.

Particular values for such parameter, however, can be selected that can lead to a particular amount of electrical stimulation therapy being provided, i.e., the target may be achieved. The electrical stimulation therapy actually provided to patient 16 may include a particular therapy target, i.e., an amount of electrical stimulation for one or more stimulation parameters, e.g., amplitude, pulse width and/or inter-stimulation interval.

An example is provided using a single stimulation parameter, namely inter-stimulation interval ("ISI"). It is to be recognized and understood, however, that the technique, apparatus and process is equally applicable to one or more of other stimulation parameters.

Instead of using a single ISI, e.g., 300 seconds, which permits cycling the delivery of electrical stimulation at equal intervals, device 10 may operate with multiple values of ISI which may be defined or generated allowing for increased flexibility in programming of electrical stimulation delivery.

Figure 3:
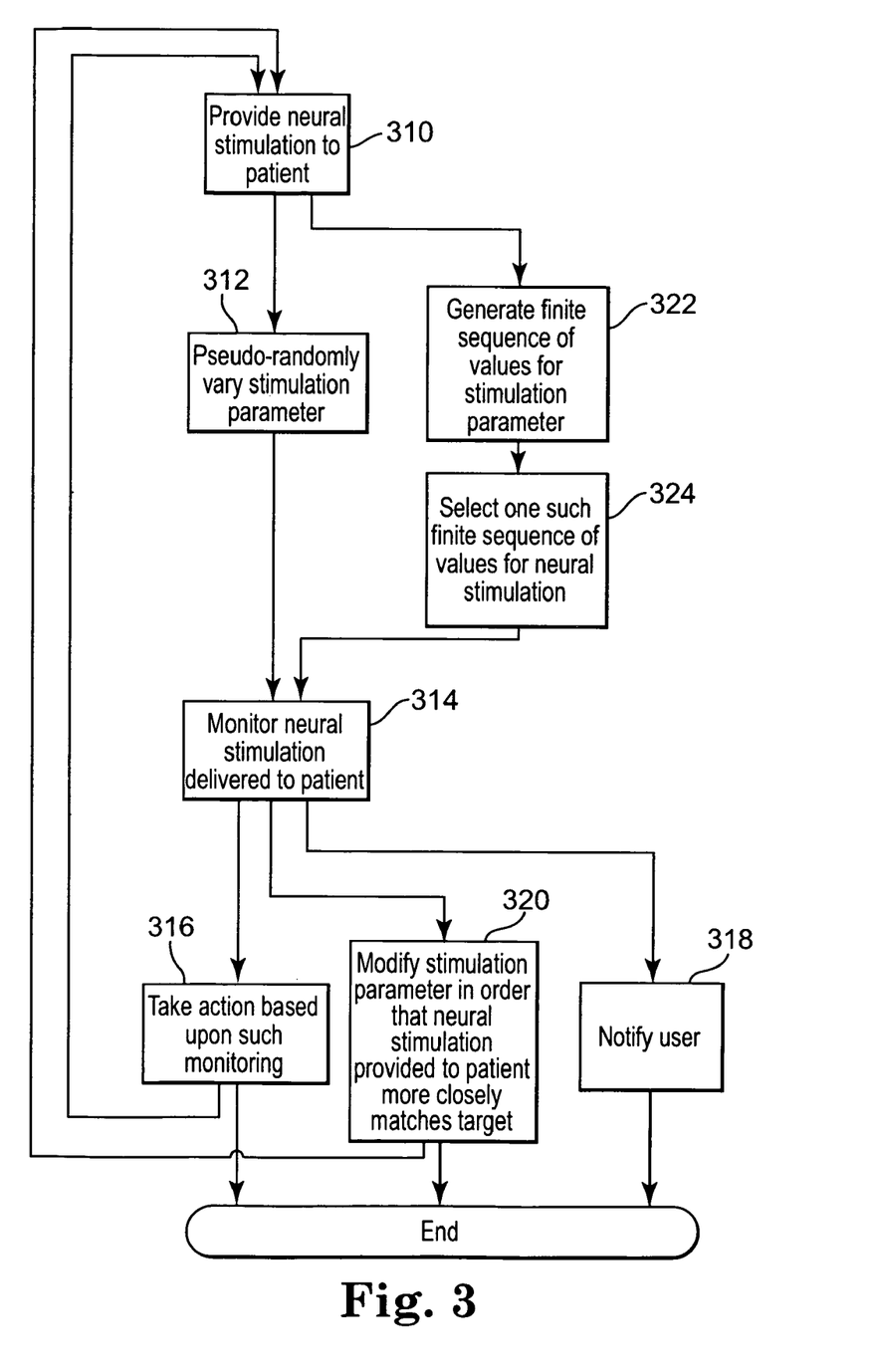
FIG. 3 is a general flow chart of the process of providing neural stimulation for the patient in accordance with an embodiment of the invention.

Described in general terms in FIG. 3, device 10 operates to provide neural stimulation (310) to patient 16. The apparatus and process may operate in either of two modes, a real-time random stimulation mode or a random stimulation using a pre-defined ISI sequence.

In real-time random stimulation mode, a stimulation parameter is pseudo-randomly varied (312). Device 10 contains a random number generator and a value for ISI is randomly generated for each upcoming period of stimulation. A physician or other medical professional may define lower and upper boundaries for acceptable ISI values, effectively determining an allowable range of values for ISI. When electrical stimulation is initiated, it may not be known what values of ISI will actually be delivered to patient 16. Following a period of electrical stimulation, the values of ISI used to actually provide electrical stimulation to patient 16 are monitored (314). An action may then be taken (316) based upon such monitoring. Once electrical stimulation has been provided for a period of time, such monitoring can determine whether or not the applicable target therapy has been achieved during the period. Optionally, the user, perhaps the medical professional or another acting under the direction of the medical professional, may be notified (318) of the actual therapy achieved. In this case, the medical professional may then take appropriate action, perhaps by adjusting the allowed range of values for the parameter to better achieve the target during the next or a subsequent period of time or perhaps to compensate for missing target during this period of time by skewing the allowed values for the parameter on the opposite side of the desired target value. Optionally, device 10 may modify the allowed range of values for the parameter (320) in order that the neural stimulation provided to patient 16 more closely matches the target value of prescribed stimulation. Again, such modification could be to simply change the allowed range parameter values, perhaps to offset the mean of the allowed range to fall on the opposite side of the desired target so that the target therapy over a longer period of time, for example over the preceding period of time and the next stimulation period of time will more closely match the target. If desired, the another period of therapy may be provided (310) to patient 16.

In manual stimulation mode, the physician, medical professional or another may define a series of particular values of ISI, the number of values defined being termed a parameter value sequence length or, in this case, an ISI sequence length. The sequence length is the number of ISI values that are defined, e.g., for example, a sequence of ten values.

The particular values for each of the ISI sequence slots may be determined, for example, by three different techniques.

In a first manual mode, the user is prompted to define (322) each ISI value in sequence. This technique permits customizable intervals and unique stimulation parameters for each stimulation period or stimulation trial. Device 10 may then check to determine whether or not the manually generated sequence values for ISI will or will likely approximate the target ISI value for the prescribed electrical stimulation therapy. In operation, device 10 may then select (324) one of the ISI sequence values for use in a particular electrical pulse stimulation series.

In a second manual mode, each ISI sequence value is generated (322) using a random number generator. Usually, the user, e.g., medical professional, defines the lower and upper boundaries for acceptable ISI values. Again, device 10 may then check to determine whether or not the manually generated sequence values for ISI will or will likely approximate the target ISI value for the prescribed electrical stimulation therapy. Again, device 10 may then select (324) one of the ISI sequence values for use in a particular electrical pulse stimulation series.

In a third manual mode, three values for ISI are specified, namely a lower boundary, an upper boundary and a target value. These values may then be randomly assigned (322) in the sequence of ISI values. Again, device 10 may then select (324) one of the ISI sequence values for use in a particular electrical pulse stimulation series.

Alternatively, the user may define an ISI target and may also define lower and upper boundaries as a percentage of the ISI target value. For example, the user may define ninety (90) seconds as the ISI target and a percentage variation of fifty percent (50%). In this case, the lower boundary would be defined as forty-five (45) seconds and the upper boundary would be defined as one hundred thirty-five (135) seconds. In yet another embodiment, the user may define a lower percentage deviation from the target ISI value, i.e., the ISI target value minus a defined percentage, that differs from an upper percentage deviation from the target ISI, i.e., the ISI target value plus a defined percentage, where the defined percentages may differ.

Also, the user may define an ISI target and may also define lower and upper boundaries as a set difference from the ISI target value. For example, the user may define ninety (90) seconds as the ISI target and a set difference deviation of thirty (30) seconds. In this case, the lower boundary would be defined as sixty (60) seconds and the upper boundary would be defined as one hundred twenty (120) seconds. In yet another embodiment, the user may define a lower difference from the target ISI value, i.e., the ISI target value minus a difference, that differs from an upper difference from the target ISI, i.e., the ISI target value plus a difference, where the defined differences vary.

Again, following a period of electrical stimulation, the values of ISI used to actually provide electrical stimulation to patient 16 are monitored (314). An action may then be taken (316) based upon such monitoring. Once electrical stimulation has been provided for a period of time, such monitoring can determine whether or not the applicable target therapy has been achieved during the period. Optionally, the user, perhaps the medical professional or another acting under the direction of the medical professional, may be notified (318) of the actual therapy achieved. In this case, the medical professional may then take appropriate action, perhaps by adjusting the allowed range of values for the parameter to better achieve the target during the next or a subsequent period of time or perhaps to compensate for missing target during this period of time by skewing the allowed values for the parameter on the opposite side of the desired target value. Optionally, device 10 may modify the allowed range of values for the parameter (320) in order that the neural stimulation provided to patient 16 more closely matches the target value of prescribed stimulation. Again, such modification could be to simply change the allowed range parameter values, perhaps to offset the mean of the allowed range to fall on the opposite side of the desired target so that the target therapy over a longer period of time, for example over the preceding period of time and the next stimulation period of time will more closely match the target. If desired, the another period of therapy may be provided (310) to patient 16.

Figure 4:
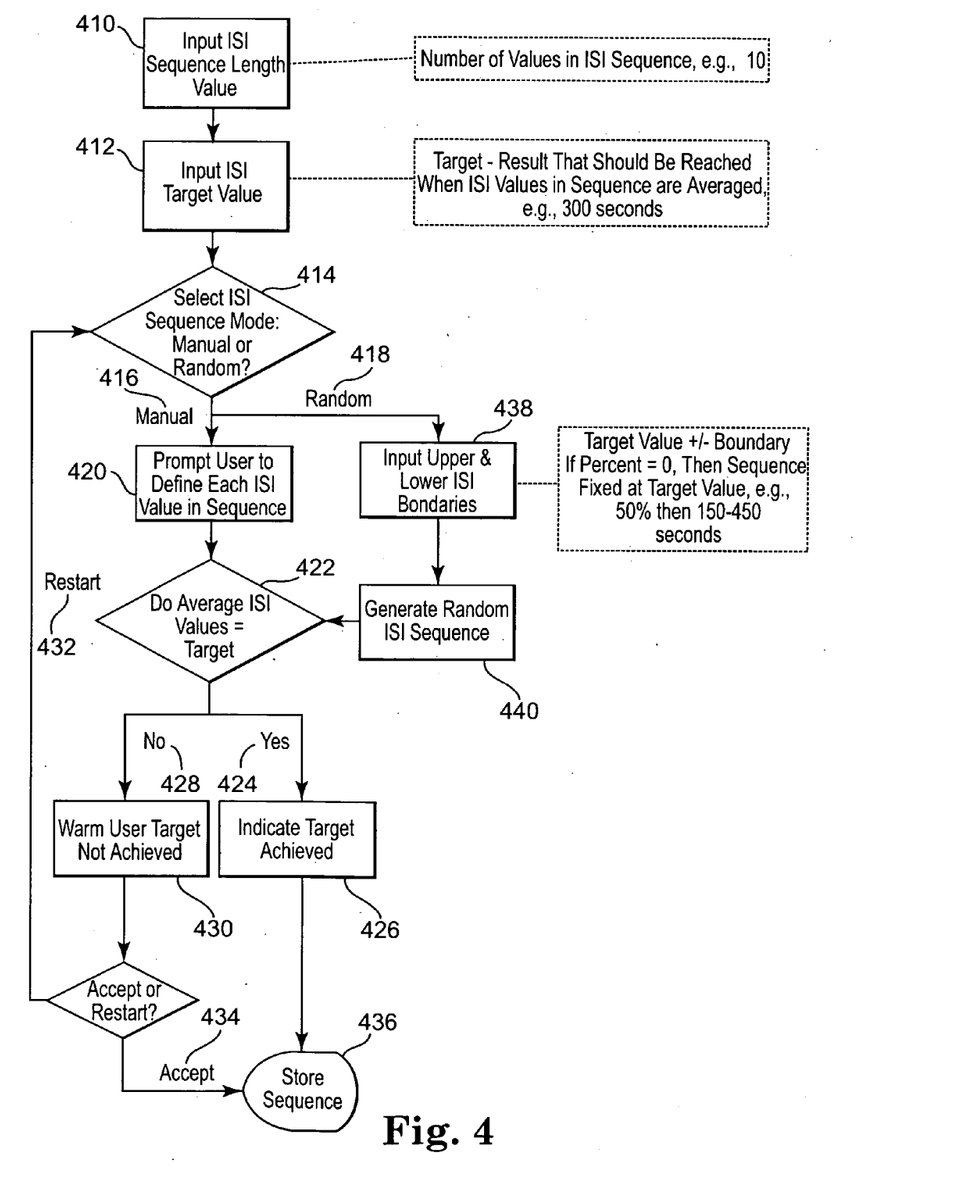
FIG. 4 is a more detailed flow chart of the process of providing neural stimulation for the patient in accordance with an embodiment of the invention.

FIG. 4 illustrates an embodiment of the apparatus (device 10) and process in more detail, again using ISI as an example of a parameter being varied. In particular, a series of values of ISI are input (410) or provided. As an example, the input could consist of a number of values in an ISI sequence, e.g., ten values. Such ISI values may be determined, for example, by the one of the techniques and methods described above with reference to FIG. 3.

An ISI target value is input (412). The target value represents the resulting electrical stimulation therapy that should be achieved provided that the target value of ISI is reached. In an example, the target could be the average of all ISI sequence values in the ISI sequence, e.g., 300 seconds.

The mode of operation of device 10 is selected (414), either manual mode (416) or random mode (418).

In manual mode (416), the user is prompted to define each ISI value in the ISI sequence (420). Device 10 then determines whether or not the average of all ISI values in the ISI sequence equals the target ISI value (422).

If the average of all ISI values in the ISI sequence equals the target ISI value (424), the user is notified (426) that the target ISI value is achieved.

If the average of all ISI value in the ISI sequence does not equal the target ISI value (428), then the user is warned (430) that the ISI target value is not achieved.

The generation and selection of ISI values may then be restarted (432) by returning to selecting either manual or random mode (414) or the ISI sequence values may be accepted (434) and the ISI sequence values stored (436) for use by stimulator section 20.

Figure 5:
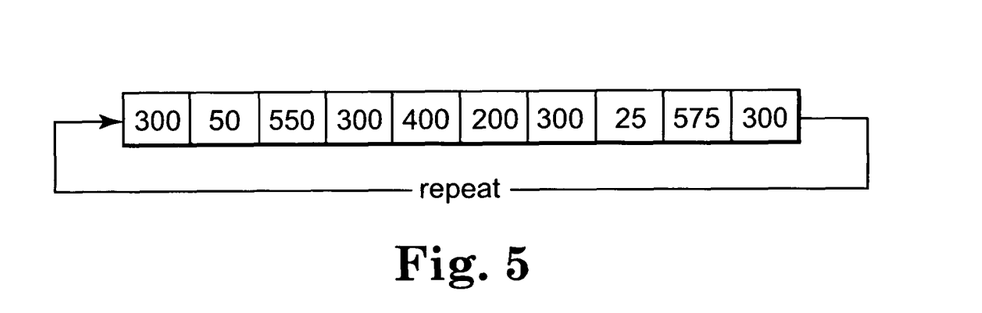
FIG. 5 is an example of a sequence of values manually generated in accordance with an aspect of an embodiment of the invention.

An example of a sequence of ISI values generated using the manual mode (416) of operation is illustrated in FIG. 5 using a mean ISI value of 300 seconds.

In random mode (418), lower and upper boundaries for ISI values are input (438). The lower and upper boundaries may be set by establishing a percent variation from the target ISI value. In this case, a zero percent (0%) variation would limit the ISI value to be fixed at the target ISI value, e.g., 300 seconds. On the other hand, a fifty percent (50%) variation could allow a range of ISI values from 150 seconds to 450 seconds, assuming a target ISI value of 300 seconds.

A sequence of ISI values is randomly generated (440) using the lower and upper boundaries and the target ISI value. Following generation of a sequence of ISI values, the process continues to determine (422) whether or not the average of all ISI values in the ISI sequence equals the target ISI value as discussed above.

Figure 6:
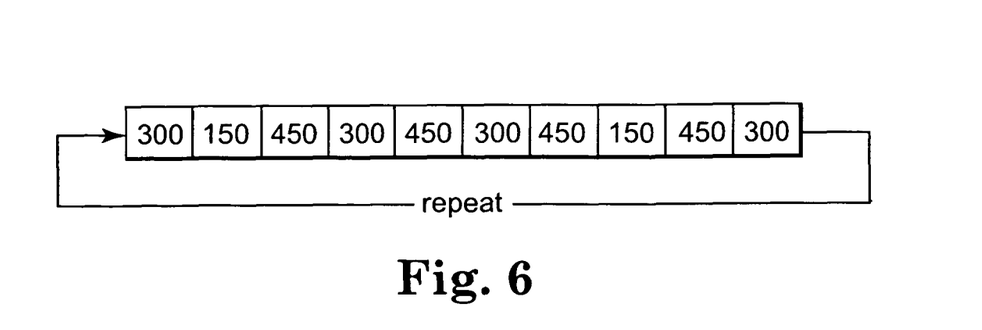
FIG. 6 is an example of a sequence of values randomly generated in accordance with an aspect of an embodiment of the invention

An example of a sequence of ISI values generated using the random mode (418) of operation is illustrated in FIG. 6 using a mean ISI value of 300 seconds.

Thus, embodiments of the method and apparatus providing asynchronous neural stimulation are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of providing neural stimulation to a patient with a neural stimulator comprising a comparator, a monitor, a stimulator configured to provide a stimulation having a plurality of stimulation parameters, and a random number generator, said neural stimulation having a target within a range of pseudo-random variation of an amount of neural stimulation for at least one of said plurality of stimulation parameters, comprising the steps of:

providing neural stimulation having said plurality of stimulation parameters with said stimulator of said neural stimulator;

pseudo-randomly varying at least one of said plurality of stimulation parameters with said random number generator;

monitoring said neural stimulation actually delivered to said patient with said monitor of said neural stimulator;

comparing said neural stimulation actually delivered to said patient with said target within said range of pseudo-random variation of said amount of neural stimulation of said at least one of said plurality of stimulation parameters with said comparator of said neural stimulator; and
said neural stimulator taking an action based upon said monitoring step.

2. A method as in claim 1 wherein said taking an action step comprises modifying at least one of said plurality of stimulation parameters in order that said neural stimulation more closely matches said target.

3. A method as in claim 1 wherein said taking an action step comprises notifying a user of a result of said monitoring step.

4. The method as in claim 1 wherein said plurality of stimulation parameters is at least two of a pulse amplitude, a pulse width and an inter-stimulation interval.

5. A method of providing neural stimulation having a plurality of stimulation parameters to a patient with a neural stimulator comprising a stimulator and a random number generator, said neural stimulation having a target of neural stimulation actually delivered within a range of pseudo-random variation of an amount of neural stimulation for at least one of said plurality of stimulation parameters, said target determined, at least in part, by said plurality of stimulation parameters, comprising the steps of:
    providing neural stimulation specified by said plurality of stimulation parameters with said stimulator of said neural stimulator;
    monitoring said neural stimulation actually delivered to said patient; and
    pseudo-randomly varying at least one of said plurality of stimulation parameters with said random number generator in a way to more closely match said target of neural stimulation actually delivered.

6. A method as in claim 5 wherein said pseudo-randomly varying step comprises the steps of:
    generating a finite sequence of values within said range of stimulation parameter values of at least one of said plurality of stimulation parameters; and
    selecting one of said finite sequence of values for said neural stimulation.

7. A method as in claim 6 wherein said range of stimulation parameter values is selected by said neural stimulator so that an average of said finite sequence of values more closely matches said target of neural stimulation actually delivered than would occur randomly.

8. A method as in claim 6 wherein said range of stimulation parameter values is selected by said neural stimulator so that an average of said finite sequence of values approximates said target of neural stimulation actually delivered.

9. A method as in claim 8 wherein said range of stimulation parameter values is selected by said neural stimulator so that said average of said finite sequence of values matches said target of neural stimulation actually delivered.

10. A method as in claim 6 wherein said selecting step is repeated during a stimulation treatment period.

11. A method as in claim 10 wherein said generating step is performed manually.

12. A method as in claim 10 wherein possible values within said range of stimulation parameter values for said values of said sequence of values are generated pseudo-randomly and wherein said selecting step is performed manually.

13. A method as in claim 5 wherein said at least one of said plurality of stimulation parameters comprises a parameter selected from the group consisting of an inter-stimulation interval, amplitude and pulse width.

* * * * *